(12) United States Patent
Kondo (10) Patent No.: US 8,444,565 B2
(45) Date of Patent: May 21, 2013

(54) ULTRASONIC DIAGNOSTIC APPARATUS, METHOD OF MEASURING PRESSURE GRADIENT, AND METHOD OF MEASURING BLOOD VESSEL ELASTICITY

(75) Inventor: Yuji Kondo, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 557 days.

(21) Appl. No.: 12/659,361

(22) Filed: Mar. 5, 2010

(65) Prior Publication Data

US 2010/0241000 A1 Sep. 23, 2010

(30) Foreign Application Priority Data

Mar. 18, 2009 (JP) .................................. 2009-066833

(51) Int. Cl.
*A61B 8/00* (2006.01)
(52) U.S. Cl.
USPC .............................. 600/454; 600/437; 600/407
(58) Field of Classification Search
USPC ................. 600/407, 437, 453–455, 457, 465, 600/468, 479–481; 382/128
See application file for complete search history.

(56) References Cited

U.S. PATENT DOCUMENTS

| 4,646,754 A * | 3/1987 | Seale ............................ 600/587 |
| 6,135,957 A * | 10/2000 | Cohen-Bacrie et al. ...... 600/438 |
| 2005/0240101 A1 * | 10/2005 | Kato et al. .................... 600/437 |

FOREIGN PATENT DOCUMENTS

| JP | 2002-209857 | 7/2002 |
| JP | 2004-041382 | 2/2004 |

* cited by examiner

*Primary Examiner* — Tse Chen
*Assistant Examiner* — Joel F Brutus
(74) *Attorney, Agent, or Firm* — Jean C. Edwards, Esq.; Edwards Neils PLLC (57) ABSTRACT

An ultrasonic diagnostic apparatus capable of obtaining information on a pressure gradient in a blood vessel based on only reception signals of ultrasonic echoes reflected within an object. The apparatus includes: an ultrasonic probe for outputting reception signals; a measuring unit for measuring an inside radius of a blood vessel within the object and blood flow velocities in plural locations in a radial direction substantially at the same time based on the reception signals; and a computing unit for computing a velocity gradient in the radial direction at an inner wall point of the blood vessel by differentiating the blood flow velocities measured by the measuring unit in the radial direction, and computing a pressure gradient at ends of a predetermined length of the blood vessel based on the computed velocity gradient, the measured inside radius of the blood vessel, and a predetermined viscosity of blood.

6 Claims, 4 Drawing Sheets

ULTRASONIC DIAGNOSTIC APPARATUS, METHOD OF MEASURING PRESSURE GRADIENT, AND METHOD OF MEASURING BLOOD VESSEL ELASTICITY

CROSS-REFERENCE TO RELATED APPLICATION

The present application claims priority from Japanese Patent Application No. 2009-066833 filed on Mar. 18, 2009, the contents of which are incorporated herein by reference in their entirety.

BACKGROUND OF THE INVENTION

1. Field of the Invention

The present invention relates to an ultrasonic diagnostic apparatus capable of obtaining information on a pressure gradient in a blood vessel or elasticity of the blood vessel based on reception signals of ultrasonic echoes reflected within an object to be inspected. The present invention further relates to a method of measuring a pressure gradient and a method of measuring blood vessel elasticity, to be used in the ultrasonic diagnostic apparatus.

2. Description of a Related Art

As indexes of blood vessel elasticity, a pulse wave velocity, a stiffness parameter β, and so on are known. In equipment in practical use, ABI (Ankle Brachial Pressure Index) measurement of measuring pulse wave propagation velocities in an arm and a foot, CAVI (Cardio Ankle Vascular Index) measurement of estimating a stiffness parameter β by using the propagation velocities, and so on are used.

However, these values are indexes weighted by fixed factors, but are not estimation of an absolute value of blood vessel elasticity. Further, for measurement of the pulse wave propagation velocities, measurement between sufficiently spaced two points is necessary and the arm and the food are selected therefor, and thus, the values do not express the elasticity of a local area of the blood vessel but only express average values in parts over significantly wide ranges. In addition, the pulse wave measurement is blood pressure measurement using a cuff (a band wrapped around an arm in a manometer), and there is a problem about stability of the measurement.

On the other hand, there has been an attempt to evaluate properties of a blood vessel by measuring IMT (Intima Media Thickness) of an artery such as a carotid artery by using ultrasonic waves. This method is simple but there is a discussion that a change of IMT appears as a result of arteriosclerosis and do not necessarily have a correlation with blood vessel elasticity.

Further, in recent years, there has been an attempt to measure blood vessel properties by FMD (Flow Mediated Dilatation) examination of measuring changes of an inside radius of an artery or IMT before and after interruption of blood flow. However, the measurement is far from simple measurement because measurement environments are strict such that it is necessary to keep a patient at rest, and blood pressure measurement must be performed at the same time with ultrasonic measurement, and so on. Although it is possible to estimate a blood vessel elastic modulus according to its definition by measuring the change of a blood vessel wall thickness such as IMT in a systolic phase and a diastolic phase, it is necessary for the purpose to know the magnitude of an applied force to change the blood vessel wall thickness. What dilates a blood vessel is its inner pressure, and therefore, it is appropriate to use the change in blood pressure as the change in force. However, blood pressure measurement must be performed at the same time with ultrasonic measurement, and an assumption is necessary that the blood pressure is internal pressure at ultrasonic measurement. As described above, the FMD examination has a problem of unreliability of measurement and a problem of complication of measurement.

As a related technology, Japanese Patent Application Publication JP-P2004-41382A discloses an ultrasonic diagnostic apparatus for more correctly measuring local blood pressure by using ultrasonic waves. The ultrasonic diagnostic apparatus includes transmitting and receiving means for transmitting and receiving ultrasonic waves to and from an object to be inspected, blood vessel size waveform information computing means for obtaining local size waveform information with respect to a specific local part in a blood vessel within the object, which information represents temporal changes of a size thereof, based on reception signals obtained by transmission and reception of ultrasonic waves, a manometer to be mounted on a body surface of the object, for measuring a systolic blood pressure and a diastolic blood pressure, and estimating means for estimating local blood pressure waveform information with respect to the specific local part, which information represents temporal changes of a local blood pressure thereof, by converting the local size waveform information based on the systolic blood pressure and the diastolic blood pressure measured by the manometer. The ultrasonic diagnostic apparatus is characterized in that the estimating means executes a computation of obtaining the local blood pressure waveform information by providing the systolic blood pressure and the diastolic blood pressure to a nonlinear function for estimating the local blood pressure waveform information from the local size waveform information.

According to JP-P2004-41382A, although the local blood pressure waveform information representing the temporal changes of the local blood pressure can be obtained based on the local size waveform information obtained with respect to the specific local part in the blood vessel within the object, it is necessary to measure the systolic blood pressure and the diastolic blood pressure by using the manometer, and the measurement becomes complicated.

Further, JP-P2002-209857A discloses a method of measuring a blood vessel elastic modulus by which a blood vessel elastic modulus is easy to be actually measured by using a manometer and an ultrasonic diagnostic apparatus and more credible blood vessel elastic modulus can be measured than a conventional one. The method of measuring a blood vessel elastic modulus includes the steps of measuring first blood pressure pi1, a blood vessel inside radius a1, and a blood vessel outside radius b1, measuring second blood pressure pi2, a blood vessel inside radius a2, and a blood vessel outside radius b2, and obtaining a blood vessel elastic modulus E according to the following expression.

$$E = [pi2\{a_2^2/(b_2^2-a_2^2)\} - pi1\{a_1^2/(b_1^2-a_1^2)\}]/\{(b_2-b_1)/(b_2+b_1)\}$$

According to JP-P2002-209857A, although the blood vessel elastic modulus can be obtained based on the two types of blood pressure and the corresponding blood vessel inside radii and blood vessel outside radii, it is necessary to measure the two types of blood pressure by using the manometer, and the measurement becomes complicated.

SUMMARY OF THE INVENTION

The present invention has been achieved in view of the above-mentioned problems. A purpose of the present invention is to provide an ultrasonic diagnostic apparatus capable of obtaining information on a pressure gradient in a blood vessel or elasticity of the blood vessel based on only reception signals of ultrasonic echoes reflected within an object to be inspected without measuring blood pressure of the object. A further purpose of the present invention is to provide a method of measuring a pressure gradient and a method of measuring blood vessel elasticity to be used in the ultrasonic diagnostic apparatus.

In order to accomplish the above-mentioned purposes, an ultrasonic diagnostic apparatus according to a first aspect of the present invention includes: an ultrasonic probe including plural ultrasonic transducers for transmitting ultrasonic waves to an object to be inspected according to drive signals, and receiving ultrasonic echoes propagating from the object to output reception signals; measuring means for measuring an inside radius of a blood vessel within the object and blood flow velocities in plural locations in a radial direction substantially at the same time based on the reception signals outputted from the ultrasonic probe; and computing means for computing a velocity gradient in the radial direction at an inner wall point of the blood vessel by differentiating the blood flow velocities measured by the measuring means in the radial direction, and computing a pressure gradient at ends of a predetermined length of the blood vessel based on the computed velocity gradient, the inside radius of the blood vessel measured by the measuring means, and a predetermined viscosity of blood.

Further, an ultrasonic diagnostic apparatus according to a second aspect of the present invention includes: an ultrasonic probe including plural ultrasonic transducers for transmitting ultrasonic waves to an object to be inspected according to drive signals, and receiving ultrasonic echoes propagating from the object to output reception signals; measuring means for measuring inside radii of a blood vessel in two locations spaced at a predetermined distance in a longitudinal direction of the blood vessel, a thickness of the blood vessel in at least one location, and blood flow velocities in plural locations in a radial direction substantially at the same time; and computing means for computing a velocity gradient in the radial direction at an inner wall point of the blood vessel by differentiating the blood flow velocities measured by the measuring means in the radial direction, and computing an elastic modulus of the blood vessel based on the computed velocity gradient, the inside radius and the thickness of the blood vessel measured by the measuring means, a difference between the inside radii of the blood vessel in the two locations, the predetermined distance, and a predetermined viscosity of blood.

A method of measuring a pressure gradient according to the first aspect of the present invention includes the steps of: (a) transmitting ultrasonic waves to an object to be inspected and receiving ultrasonic echoes propagating from the object by using an ultrasonic probe including plural ultrasonic transducers, and thereby, measuring an inside radius of a blood vessel within the object and blood flow velocities in plural locations in a radial direction substantially at the same time; and (b) computing a velocity gradient in the radial direction at an inner wall point of the blood vessel by differentiating the blood flow velocities measured at step (a) in the radial direction, and computing the pressure gradient at ends of a predetermined length of the blood vessel based on the computed velocity gradient, the inside radius of the blood vessel measured at step (a), and a predetermined viscosity of blood.

Further, a method of measuring blood vessel elasticity according to the second aspect of the present invention includes the steps of: (a) transmitting ultrasonic waves to an object to be inspected and receiving ultrasonic echoes propagating from the object by using an ultrasonic probe including plural ultrasonic transducers, and thereby, measuring inside radii of a blood vessel in two locations spaced at a predetermined distance in a longitudinal direction of the blood vessel, a thickness of the blood vessel in at least one location, and blood flow velocities in plural locations in a radial direction substantially at the same time; and (b) computing a velocity gradient in the radial direction at an inner wall point of the blood vessel by differentiating the blood flow velocities measured at step (a) in the radial direction, and computing the elastic modulus of the blood vessel based on the computed velocity gradient, the inside radius and the thickness of the blood vessel measured at step (a), a difference between the inside radii of the blood vessel in the two locations, the predetermined distance, and a predetermined viscosity of blood.

According to the first aspect of the present invention, the pressure gradient at the ends of the predetermined length of the blood vessel can be computed by receiving ultrasonic echoes propagating from the object and measuring the inside radius of the blood vessel within the object and the blood flow velocities in the plural locations in the radial direction substantially at the same time. Further, according to the second aspect of the present invention, the elastic modulus of the blood vessel can be computed by receiving ultrasonic echoes propagating from the object and measuring the inside radii of the blood vessel in the two locations spaced at the predetermined distance in the longitudinal direction of the blood vessel, the thickness of the blood vessel in the at least one location, and the blood flow velocities in the plural locations in the radial direction substantially at the same time.

DESCRIPTION OF THE PREFERRED EMBODIMENTS

Hereinafter, embodiments of the present invention will be explained in detail with reference to the drawings.

Figure 1:
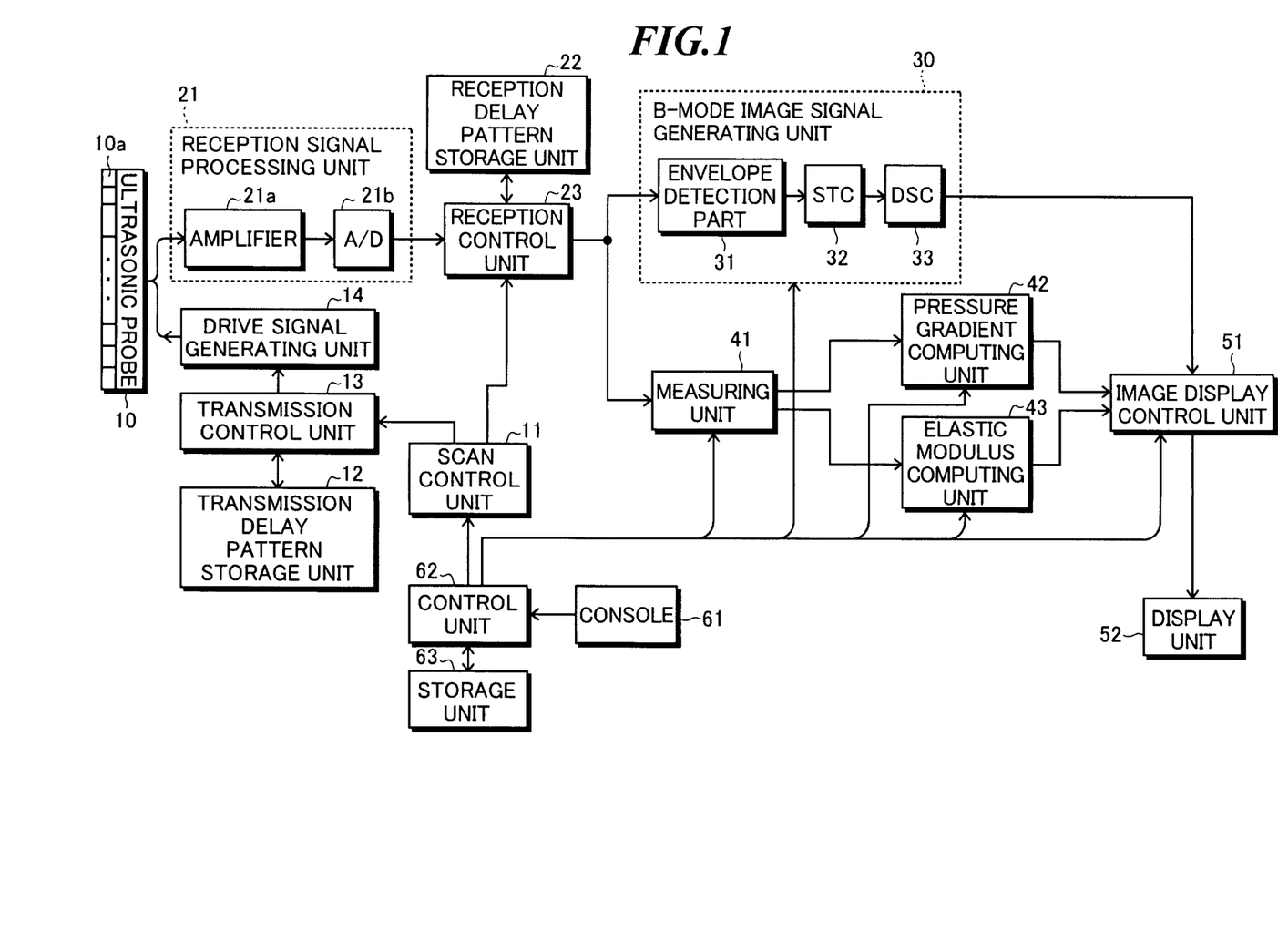
FIG. 1 is a block diagram showing a configuration of an ultrasonic diagnostic apparatus according to one embodiment of the present invention.

FIG. 1 is a block diagram showing a configuration of an ultrasonic diagnostic apparatus according to one embodiment of the present invention. The ultrasonic diagnostic apparatus includes an ultrasonic probe 10, a scan control unit 11, a transmission delay pattern storage unit 12, a transmission control unit 13, a drive signal generating unit 14, a reception signal processing unit 21, a reception delay pattern storage unit 22, a reception control unit 23, a B-mode image signal generating unit 30, a measuring unit 41, a pressure gradient computing unit 42, an elastic modulus computing unit 43, an image display control unit 51, a display unit 52, a console 61, a control unit 62, and a storage unit 63.

The ultrasonic probe 10 includes plural ultrasonic transducers 10a forming a one-dimensional or two-dimensional transducer array. These ultrasonic transducers 10a transmit ultrasonic waves toward an object to be inspected according to applied drive signals, and receive ultrasonic echoes propagating from the object to output reception signals.

Each ultrasonic transducer 10a includes a vibrator having electrodes formed on both ends of a material having a piezoelectric property (piezoelectric material) such as a piezoelectric ceramic represented by PZT (Pb (lead) zirconate titanate), a polymeric piezoelectric element represented by PVDF (polyvinylidene difluoride), or the like. When a pulsed or continuous wave voltage is applied to the electrodes of the vibrator, the piezoelectric material expands and contracts. By the expansion and contraction, pulse or continuous wave ultrasonic waves are generated from the respective vibrators, and an ultrasonic beam is formed by synthesizing these ultrasonic waves. Further, the respective vibrators expand and contract by receiving the propagating ultrasonic waves to generate electric signals. These electric signals are outputted as reception signals of ultrasonic waves.

The scan control unit 11 sequentially sets transmission directions of ultrasonic beams and reception directions of ultrasonic echoes. The transmission delay pattern storage unit 12 to the reception control unit 23 form signal processing means for supplying drive signals to the plural ultrasonic transducers 10a and performing reception focusing processing on the reception signals outputted from the plural ultrasonic transducers 10a to generate sound ray signals along reception directions of ultrasonic waves.

The transmission delay pattern storage unit 12 stores plural transmission delay patterns to be used when ultrasonic beams are formed. The transmission control unit 13 selects one transmission delay pattern from plural transmission delay patterns stored in the transmission delay pattern storage unit 12 according to transmission directions set by the scan control unit 11, and sets delay times to be respectively provided to the drive signals for the plural ultrasonic transducers 10a based on the selected transmission delay pattern.

The drive signal generating unit 14 includes plural pulsers corresponding to the plural ultrasonic transducers 10a, for example. The drive signal generating unit 14 supplies drive signals to the ultrasonic probe 10 such that the ultrasonic waves transmitted from the plural ultrasonic transducers 10a form ultrasonic beams.

The reception signal processing unit 21 includes plural amplifiers (preamplifiers) 21a and plural A/D converters 21b corresponding to the plural ultrasonic transducers 10a. The reception signals outputted from the ultrasonic transducers 10a are amplified by the amplifiers 21a, and analog reception signals outputted from the amplifiers 21a are converted into digital reception signals by the A/D converters 21b. The A/D converters 21b output the digital reception signals to the reception control unit 23.

The reception delay pattern storage unit 22 stores plural reception delay patterns to be used when reception focusing processing is performed on the reception signals outputted from the plural ultrasonic transducers 10a. The reception control unit 23 selects one reception delay pattern from the plural reception delay patterns stored in the reception delay pattern storage unit 22 according to the reception directions set by the scan control unit 11, and performs reception focusing processing by providing delays to the reception signals based on the selected reception delay pattern and adding the reception signals to one another. By the reception focusing processing, reception signals (sound ray signals) in which the focus of the ultrasonic echoes is narrowed are formed.

The B-mode image signal generating unit 30 generates a B-mode image signal as tomographic image information on tissues within the object based on the sound ray signals generated by the reception control unit 23. For the purpose, the B-mode image signal generating unit 30 includes an envelope detection part 31, an STC (sensitivity time control) part 32, and a DSC (digital scan converter) 33.

The envelope detection part 31 performs envelope detection processing on the sound ray signals generated by the reception control unit 23. The STC part 32 performs attenuation correction by distance on the sound ray signals subjected to envelope detection processing by the envelope detection part 31, according to the depths of the reflection positions of ultrasonic waves. The DSC 33 converts (raster-converts) the sound ray signals corrected by the STC part 32 into an image signal that follows the normal scan system of television signals, and performs necessary image processing such as gradation processing to generate a B-mode image signal.

The measuring unit 41 to the elastic modulus computing unit 43 obtain information on a pressure gradient in a blood vessel or elasticity of the blood vessel based on reception signals outputted from the ultrasonic probe 10. In the embodiment, the sound ray signals generated by the signal processing means based on the reception signals outputted from the ultrasonic probe 10 are used.

When the pressure gradient is measured, the measuring unit 41 measures an inside radius of a blood vessel within the object and blood flow velocities in plural locations in a radial direction substantially at the same time by using the sound ray signals outputted from the reception control unit 23. Here, "substantially at the same time" tolerates a time difference to the degree that the ultrasonic beam transmitted from the ultrasonic probe 10 can scan plural locations in the radial direction within the blood vessel. The blood flow velocities are measured by using an ultrasonic Doppler method.

The pressure gradient computing unit 42 computes a velocity gradient in the radial direction at an inner wall point of the blood vessel by differentiating the blood flow velocities measured by the measuring unit 41 in the radial direction, and computes the pressure gradient at ends of a predetermined length of the blood vessel based on the computed velocity gradient, the inside radius of the blood vessel measured by the measuring unit 41, and a predetermined viscosity of blood. The computing method will be explained later in detail.

Further, when the elastic modulus of the blood vessel is measured, the measuring unit 41 measures inside radii in two locations spaced at a predetermined distance in a longitudinal direction of the blood vessel, a thickness of the blood vessel in at least one location, and blood flow velocities in plural locations in the radial direction substantially at the same time by using the sound ray signals outputted from the reception control unit 23. Here, "substantially at the same time" tolerates a time difference to the degree that the ultrasonic beam transmitted from the ultrasonic probe 10 can scan plural locations in the radial direction within the blood vessel. The blood flow velocities are measured by using the ultrasonic Doppler method.

The elastic modulus computing unit 43 computes a velocity gradient in the radial direction at an inner wall point of the blood vessel by differentiating the blood flow velocities measured by the measuring unit 41 in the radial direction, and computes the elastic modulus of the blood vessel based on the computed velocity gradient, the inside radius and the thickness of the blood vessel measured by the measuring unit 41, a difference between the inside radii in the two locations, the predetermined distance, and a predetermined viscosity of blood. The computing method will be explained later in detail.

Figure 2:
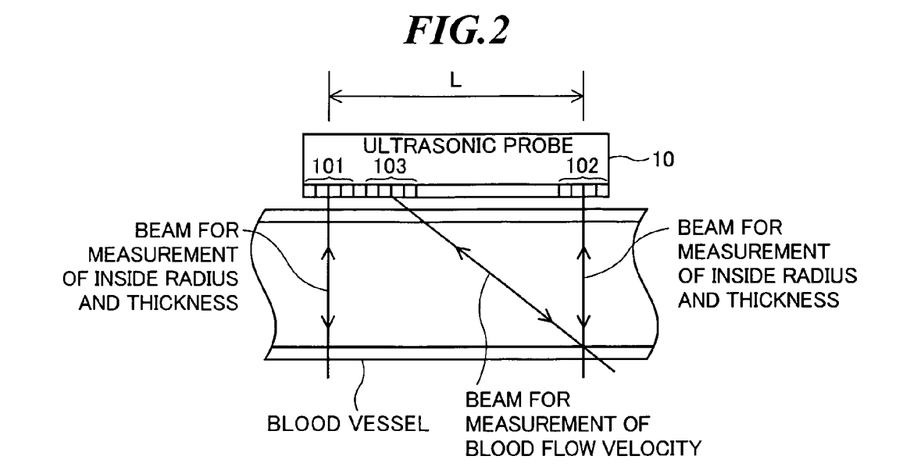
FIG. 2 shows measurement of an elastic modulus of a blood vessel using the ultrasonic diagnostic apparatus according to the one embodiment of the present invention.

FIG. 2 shows measurement of an elastic modulus of a blood vessel using the ultrasonic diagnostic apparatus according to the one embodiment of the present invention. As shown in FIG. 2, the ultrasonic probe 10 has linearly arranged ultrasonic transducers. Among them, a first group of ultrasonic transducers 101 and a second group of ultrasonic transducers 102 spaced at a predetermined distance "L", and a third group of ultrasonic transducers 103 are used.

The first group of ultrasonic transducers 101 and the second group of ultrasonic transducers 102 simultaneously transmit and receive ultrasonic waves to form ultrasonic beams for measurement of inside radius and thickness of the blood vessel in the two locations spaced at the predetermined distance "L". Further, the third group of ultrasonic transducers 103 transmit and receive ultrasonic waves to sequentially form oblique ultrasonic beams for measurement of blood flow velocity in plural locations in the radial direction within the blood vessel, and the ultrasonic beams are used as Doppler beams for Doppler blood flow measurement.

Figure 3:
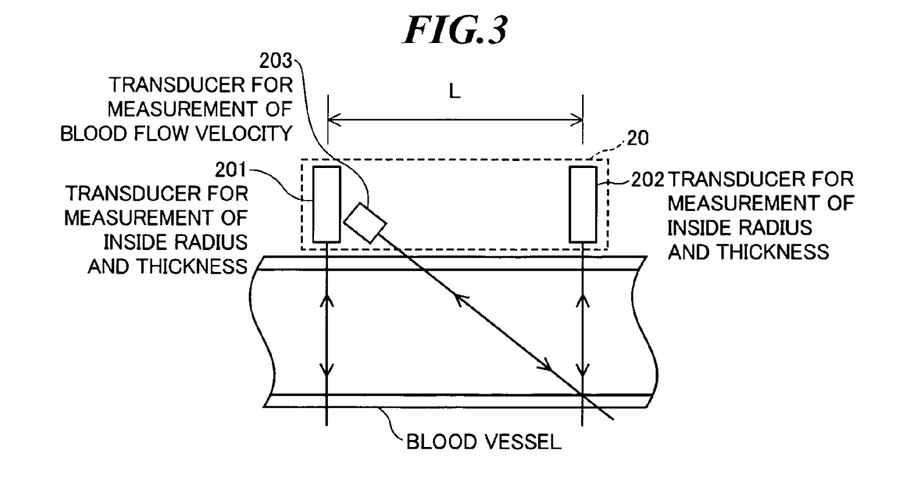
FIG. 3 shows measurement of an elastic modulus of a blood vessel using the ultrasonic diagnostic apparatus according to a modified example of the one embodiment of the present invention.

FIG. 3 shows measurement of an elastic modulus of a blood vessel using the ultrasonic diagnostic apparatus according to a modified example of the one embodiment of the present invention. In FIG. 2, the arranged ultrasonic transducers are used, but the arranged ultrasonic transducers are not necessarily required for elastic modulus measurement of a blood vessel. Accordingly, in the modified example, for elastic modulus measurement of the blood vessel, an ultrasonic probe 20 including three ultrasonic transducers 201-203 is used. In this case, the B-mode image signal generating unit 30 for generating a B-mode image signal as shown in FIG. 1, and so on become unnecessary.

As shown in FIG. 3, the first ultrasonic transducer 201 and the second ultrasonic transducer 202 transmit and receive ultrasonic waves for measurement of inside radius and thickness of the blood vessel in the two locations spaced at a predetermined distance "L". Further, the third ultrasonic transducer 203 is for Doppler blood flow measurement, and transmits and receives ultrasonic waves for measurement of blood flow velocity. In order to scan the plural locations in the radial direction within the blood vessel by using ultrasonic waves, for example, the angle of the third ultrasonic transducer 203 may be sequentially changed.

Referring to FIG. 1 again, the image display control unit 51 selects at least one of the B-mode image signal generated by the B-mode image signal generating unit 30, a computation result of the pressure gradient computing unit 42, and a computation result of the elastic modulus computing unit 43, according to an operation by an operator using the console 61, and generates an image signal for display. The display unit 52 includes a display device such as a CRT, LCD, or the like, for example, and displays an ultrasonic image or a computation result based on the image signal for display.

The control unit 62 controls the scan control unit 11, the B-mode image signal generating unit 30, the measuring unit 41, and so on according to an operation by the operator using the console 61. In the embodiment, the scan control unit 11, the transmission control unit 13, the reception control unit 23 to the image display control unit 51, and the control unit 62 are formed of a CPU and software (program), but the units may be formed of digital circuits or analog circuits. The software (program) is stored in the storage unit 63. As a recording medium in the storage unit 63, not only a built-in hard disk but also a flexible disk, MO, MT, RAM, CD-ROM, DVD-ROM, or the like may be used.

Next, the method of measuring a pressure gradient to be used in the ultrasonic diagnostic apparatus as shown in FIG. 1 will be explained in detail.

Figure 4:
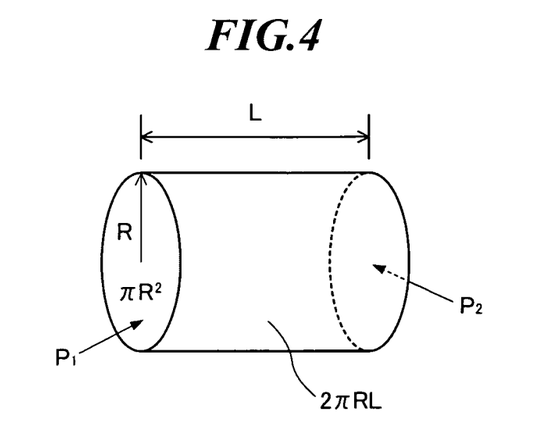
FIG. 4 is a schematic diagram for explanation of computing shear stress on a vessel wall.

FIG. 4 is a schematic diagram for explanation of computing shear stress on a vessel wall. Given that the length of the vessel is "L", the radius (inside radius) of the vessel is "R", and pressure applied on ends of the length "L" are $P_1$ and $P_2$ respectively, it is conceivable that the shear stress "$\tau$" applied on the vessel inner wall is generated when the difference between forces applied on the ends of the vessel acts on the inner wall surface of the vessel, and the shear stress is given by the following equation (1).

$$\tau = \frac{\pi R^2 (P_1 - P_2)}{2\pi R L} = \frac{R \Delta P}{2L} \tag{1}$$

where $\Delta P$ represents a pressure gradient (pressure difference) at ends of the vessel having the length "L".

On the other hand, when a viscous fluid having viscosity "$\mu$" flows in the vessel, the shear stress within the fluid is given by a product of a viscosity coefficient and a shear velocity (i.e., velocity gradient), and the following equation (2) holds. Here, "u" represents a flow velocity of the fluid, and "r" represents displacement in the radial direction of the vessel.

$$\tau = \mu \frac{du}{dr} \tag{2}$$

Thereby, in the vessel having a radius "R" in which the viscous fluid flows, the shear stress of the inner wall is expressed by replacing r=R in the equation (2). Therefore, from the equations (1) and (2), the following equation (3) is obtained.

$$\tau = \left( \mu \frac{du}{dr} \right)_{r=R} = R \frac{\Delta P}{2L} \tag{3}$$

From the equation (3), the following equation (4) is obtained.

$$\Delta P = \frac{2L\mu}{R} \left( \frac{du}{dr} \right)_{r=R} \tag{4}$$

The blood flow can be considered as an incompressible viscous flow, and the equation (4) can be applied to the blood vessel. The blood vessel radius "R" can be easily measured by an ultrasonic imaging method. Further, the velocity gradient can be easily computed by differentiating the blood flow velocities measured by the ultrasonic Doppler method in the radial direction of the vessel. That is, a flow velocity differential value may be computed on the inner wall surface or the inner wall point of the blood vessel. In this manner, the pressure gradient $\Delta P$ at ends of the blood vessel having the predetermined length "L" can be obtained as a function of the viscosity "$\mu$" of blood based on the measurement values obtained by using ultrasonic waves. The viscosity "$\mu$" of blood can be given as a constant number.

The method of measuring the pressure gradient according the above-mentioned principle is as follows. First, at step (a), the ultrasonic diagnostic apparatus transmits ultrasonic waves to the object and receives ultrasonic echoes propagating from the object by using the ultrasonic probe including the plural ultrasonic transducers, and the measuring unit 41 measures an inside radius of a blood vessel within the object and blood flow velocities in plural locations in a radial direction substantially at the same time.

Then, at step (b), the pressure gradient computing unit 42 computes a velocity gradient in the radial direction at an inner wall point of the blood vessel by differentiating the blood flow velocities measured at step (a) in the radial direction, and computes the pressure gradient at ends of a predetermined length of the blood vessel based on the computed velocity gradient, the inside radius of the blood vessel measured at step (a), and a predetermined viscosity of blood. That is, given that the blood flow velocity is "u", the displacement in the radial direction of the blood vessel is "r", the inside radius of the blood vessel is "R", the predetermined length of the blood vessel is "L", and the viscosity of blood is "μ", the measuring unit 41 computes the pressure gradient ΔP at ends of the predetermined length "L" according to the equation (4).

Next, the method of measuring blood vessel elasticity to be used in the ultrasonic diagnostic apparatus as shown in FIG. 1 will be explained in detail. Here, the case where the blood flow is pulsating is considered.

Figure 5A:
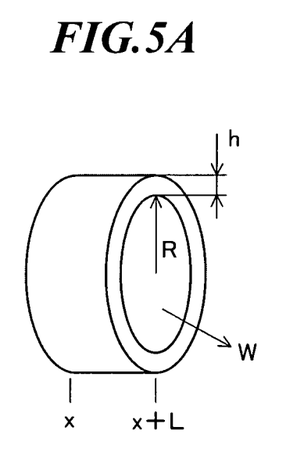
FIGS. 5A and 5B show a change of inner pressure and a change of an inside radius of an elastic vessel.
Figure 5B:
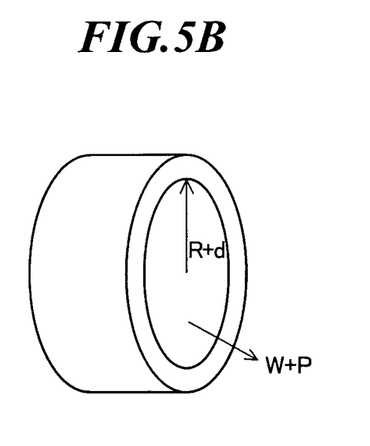

FIGS. 5A and 5B show a change of inner pressure and a change of an inside radius of an elastic vessel. Regarding the elastic vessel, given that the radius is "R", the thickness of the vessel wall is "h", and the elastic modulus (Young's modulus) is "E", the propagation of pulse wave in the elastic vessel is considered. It is assumed that, in the vessel having a radius "R" and inner pressure "W" at a certain time as shown in FIG. 5A, the inner pressure becomes (W+P) and the radius increases to (R+d) after "t" seconds as shown in FIG. 5B. It is considered that a longitudinal direction of the vessel is "x" and the change of inner pressure "P" has a gradient in the x-direction in the process to the time "t". In this case, the pressure gradient of (∂P/∂x)L is generated between the front surface and the rear surface of the layer having a length "L", and this becomes pressure that moves blood.

Figure 6A:
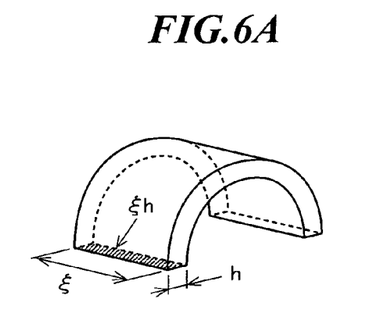
FIGS. 6A and 6B are diagrams for explanation of force equilibrium corresponding to change of inner pressure of the elastic vessel.

FIGS. 6A and 6B are diagrams for explanation of force equilibrium corresponding to change of inner pressure of the elastic vessel. In consideration of the section (hatched part) as shown in FIG. 6A, the force acting on the section of the vessel wall for extension rate of the radius d/R is (d/R) E per unit area. Since the section is pulled in a vertical direction, the tensile force $F_p$ acting on the section is expressed by the following equation (5) where the length of the elastic vessel is "ξ".

$$F_p = 2h\xi \frac{d}{R} E \tag{5}$$

Figure 6B:
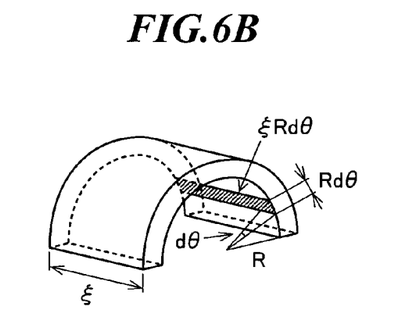

On the other hand, as shown in FIG. 6B, in consideration of an inner surface having an area of ξRdθ (hatched part) on the inner wall surface of the elastic vessel, the force $F_0$ acting on the inner surface is expressed by the following equation (6) where the pressure acting on the inner surface is "q".

$$F_0 = q\xi R d\theta \tag{6}$$

Here, the force $F_r$ that pulls apart the section having an area of ξh is force acting in the sinθ direction, and the force $F_r$ is expressed by the following equation (7).

$$F_r = \int_0^\pi F_0 \sin\theta d\theta = q\xi R \int_0^\pi \sin\theta d\theta = 2q\xi R \tag{7}$$

The force $F_r$ that pulls apart the section and the tensile force $F_p$ acting on the section are balanced as $F_r = F_p$, and therefore, the following equation (8) holds.

$$q = \frac{Ehd}{R^2} \tag{8}$$

Here, "q" is inner pressure that acts to extend the inside radius, and must be equal to the pressure increment "P" at the time "t". Therefore, the following equation (9) holds.

$$P = \frac{Ehd}{R^2} \tag{9}$$

By differentiating the equation (9), the following equation (10) is obtained.

$$\frac{\partial P}{\partial x} = \frac{Eh}{R^2} \cdot \frac{\partial d}{\partial x} \tag{10}$$

In the above description, it is assumed that the change of blood vessel inner pressure "P" and the change of the inside radius "d" are amounts of changes in the process to the time "t". However, if the time is fixed and the respective change relationships with respect to the vessel length direction "x" are considered, the equation (10) holds. Here, the wall thickness "h" becomes also a function of "x", but the wall thickness "h" is considered as a constant because the amount of change of the wall thickness "h" is extremely small compared to the change of the inside radius "d". By integrating the equation (10) with respect to the length "L", the following equation (11) is obtained.

$$\int_0^L \frac{\partial P}{\partial x} dx = \frac{Eh}{R^2} \int_0^L \frac{\partial d}{\partial x} dx \tag{11}$$

Therefore, the following equation (12) is obtained.

$$\Delta P = \frac{Eh}{R^2} \Delta d \tag{12}$$

Here, ΔP represents a pressure gradient at ends of the length "L", and Δd represents a difference between inside radii at ends of the length "L".

By substituting the equation (4) into the equation (12), the following equation (13) is obtained.

$$\frac{Eh\Delta d}{R^2} = \frac{2L\mu}{R} \left( \frac{du}{dr} \right)_{r=R} \tag{13}$$

By transforming the equation (13), the following equation (14) is obtained.

$$E = \frac{2\mu LR}{h\Delta d}\left(\frac{du}{dr}\right)_{r=R} \quad (14)$$

Figure 7A:
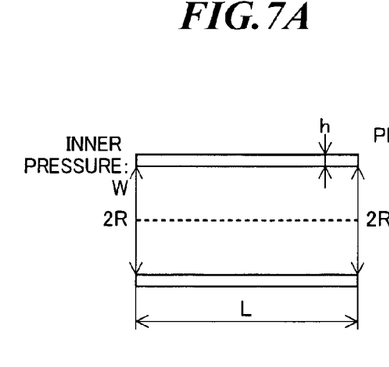
FIGS. 7A and 7B are diagrams for explanation of items to be used for computing the elastic modulus of the blood vessel.
Figure 7B:
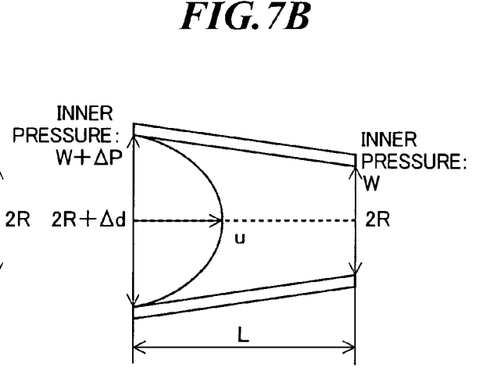

FIGS. 7A and 7B are diagrams for explanation of items to be used for computing the elastic modulus of the blood vessel. FIG. 7A shows a state where the blood vessel has a uniform inside radius. On the other hand, FIG. 7B shows a state where an end of the blood vessel bulges. This is caused by the pressure rise due to pulsation. As shown in FIG. 7B, in the first location on the right side in the drawing, the inner diameter of the blood vessel is represented by 2R, and the inner pressure is represented by "W". This shows that the pressure rise due to pulsation has not yet reached the location. On the other hand, in the second location on the left side in the drawing spaced at a predetermined distance "L" from the first location in the upstream direction of the blood flow, the inner diameter of the blood vessel is represented by (2R+Δd), and the inner pressure is represented by (W+ΔP). Further, the blood flow velocity in the second location is represented by "u".

Here, in a strict sense, the blood vessel radius "R" varies depending on the location of the blood vessel, and the shear stress applied on the blood vessel wall also varies depending on the location. Therefore, intrinsically, as the shear velocity in the equation (14), it is necessary to take an average value in the blood vessel part having the length "L". Given that the sectional area of the blood vessel is "A", the following equation (15) of continuity holds in the blood vessel part.

$$\frac{\partial A}{\partial t} + \frac{\partial}{\partial x}(uA) = 0 \quad (15)$$

The sectional area "A" becomes the maximum at a time when the change of pressure ΔP becomes the maximum, and the temporal change of the sectional area is zero. Therefore, at that time, the following equation (16) holds.

$$\frac{\partial}{\partial x}(uA) = 0 \quad (16)$$

That is, the blood flow velocity is in inverse proportion to the change of blood vessel sectional area. On the right side in FIG. 7B, the blood flow velocity increases by the amount of decrease of the sectional area caused due to the difference Δd between the blood vessel diameters. However, the difference between the sectional areas is at most several percents and the difference between the blood flow velocities is also not large, and therefore, it is considered that the difference between shear velocities on the blood vessel inner wall depending on the locations is small. Therefore, when the shear velocity on the blood vessel wall is obtained near the center of the length "L", it may be considered to give average shear stress in the length "L".

The method of measuring blood vessel elasticity based on the above-mentioned principle is as follows. First, at step (a), the ultrasonic diagnostic apparatus transmits ultrasonic waves to the object and receives ultrasonic echoes propagating from the object by using the ultrasonic probe, and the measuring unit 41 measures inside radii in two locations spaced at a predetermined distance in a longitudinal direction of the blood vessel, a thickness of the blood vessel in at least one location, and blood flow velocities in plural locations in the radial direction substantially at the same time.

Then, at step (b), the elastic modulus computing unit 43 computes a velocity gradient in the radial direction at an inner wall point of the blood vessel by differentiating the blood flow velocities measured at step (a) in the radial direction, and computes the elastic modulus of the blood vessel based on the computed velocity gradient, the inside radius and the thickness of the blood vessel measured at step (a), a difference between the inside radii of the blood vessel in the two locations, the predetermined distance, and a predetermined viscosity of blood. That is, given that the blood flow velocity is "u", the displacement in the radial direction of the blood vessel is "r", the thickness of the blood vessel is "h", the inside radius of the blood vessel is "R", the difference between the inside radii of the blood vessel in two locations is Δd, the predetermined distance is "L", and the viscosity of blood is "μ", the elastic modulus computing unit 43 computes the elastic modulus of the blood vessel "E" according to the equation (14).

Further, in order to improve the estimation accuracy of the blood vessel elasticity, it is necessary to select the time when the difference between the inside radii (the amount of change of the inside radius) of the blood vessel Δd becomes as large as possible. That is, the time is considered as the time when the pressure gradient ΔP becomes the maximum, and the time is the same as the time when the velocity gradient becomes the maximum and can be estimated from the Doppler blood flow measurement value. That is, while the velocity gradient on the vessel wall is measured in actual time, a measurement value of the blood vessel inside radius at the time when the velocity gradient becomes the maximum in a predetermined period may be used.

Specifically, the elastic modulus computing unit 43 computes the velocity gradient based on the blood flow velocities repeatedly measured by the measuring unit 41, and computes, when the velocity gradient becomes the maximum at a certain time in the predetermined period, the elastic modulus of the blood vessel based on the velocity gradient, the inside radius and the thickness of the blood vessel measured at the time, the difference between the inside radii of the blood vessel in two locations measured at the time, the predetermined distance, and the predetermined viscosity of blood.

Further, when the pressure gradient ΔP at ends of the predetermined length "L" becomes the maximum, it is conceivable that the difference Δd between the inside radii of the blood vessel at ends also becomes the maximum. Therefore, it is also effective for improving blood vessel elasticity accuracy to obtain the velocity gradient when the difference Δd between the inside radii of the blood vessel becomes the maximum.

Specifically, the elastic modulus computing unit 43 computes the difference between the inside radii of the blood vessel based on the inside radii of the blood vessel repeatedly measured in two locations by the measuring unit 41, and computes, when the difference between the blood vessel inside radii becomes the maximum at a certain time in the predetermined period, the elastic modulus of the blood vessel based on the difference between the inside radii of the blood vessel, the inside radius and the thickness of the blood vessel measured at the time, the velocity gradient computed from the blood flow velocities measured at the time, the predetermined distance, and the predetermined viscosity of blood.

According to the method of measuring blood vessel elasticity explained above, the blood vessel elasticity can be estimated only by the ultrasonic examination without measurement of the blood pressure. In addition, the measurement is extremely simple and requires none of pre-processing and post-processing.

The invention claimed is:

1. An ultrasonic diagnostic apparatus comprising:

an ultrasonic probe including plural ultrasonic transducers for transmitting ultrasonic waves to an object to be inspected according to drive signals, and receiving ultrasonic echoes propagating from the object to output reception signals;

measuring means for measuring an inside radius of a blood vessel within the object and blood flow velocities in plural locations in a radial direction substantially at the same time based on the reception signals outputted from said ultrasonic probe; and computing means for computing a velocity gradient in the radial direction at an inner wall point of the blood vessel by differentiating the blood flow velocities measured by said measuring means in the radial direction, and computing a pressure gradient at ends of a predetermined length of the blood vessel based on the computed velocity gradient, the inside radius of the blood vessel measured by said measuring means, and a predetermined viscosity of blood, wherein said measuring means computes the pressure gradient ΔP at the ends of the predetermined length "L" of the blood vessel according to the following equation:

$$\Delta P = \frac{2L\mu}{R}\left(\frac{du}{dr}\right)_{r=R}$$

where "u" represents a blood flow velocity, "r" represents displacement in the radial direction of the blood vessel, "R" represents the inside radius of the blood vessel, and "μ" represents the predetermined viscosity of blood.

2. An ultrasonic diagnostic apparatus comprising:

an ultrasonic probe including plural ultrasonic transducers for transmitting ultrasonic waves to an object to be inspected according to drive signals, and receiving ultrasonic echoes propagating from the object to output reception signals;

measuring means for measuring inside radii of a blood vessel in two locations spaced at a predetermined distance in a longitudinal direction of the blood vessel, a thickness of the blood vessel in at least one location, and blood flow velocities in plural locations in a radial direction substantially at the same time; and computing means for computing a velocity gradient in the radial direction at an inner wall point of the blood vessel by differentiating the blood flow velocities measured by said measuring means in the radial direction, and computing an elastic modulus of the blood vessel based on the computed velocity gradient, the inside radius and the thickness of the blood vessel measured by said measuring means, a difference between the inside radii of the blood vessel in the two locations, the predetermined distance, and a predetermined viscosity of blood, wherein said computing means computes the elastic modulus "E" of the blood vessel according to the following equation:

$$E = \frac{2\mu LR}{h\Delta d}\left(\frac{du}{dr}\right)_{r=R}$$

where "u" represents the blood flow velocity, "r" represents displacement in the radial direction of the blood vessel, "h" represents the thickness of the blood vessel, "R" represents the inside radius of the blood vessel, Δd represents the difference between inside radii of the blood vessel in the two locations, "L" represents the predetermined length, and "μ" represents the predetermined viscosity of blood.

3. The ultrasonic diagnostic apparatus according to claim 2, wherein said computing means computes the velocity gradient based on the blood flow velocities repeatedly measured by said measuring means, and computes, when the velocity gradient becomes a maximum at a certain time in a predetermined period, the elastic modulus of the blood vessel based on the velocity gradient, the inside radius and the thickness of the blood vessel measured at the certain time, the difference between the inside radii of the blood vessel in the two locations measured at the certain time, the predetermined distance, and the predetermined viscosity of blood.

4. The ultrasonic diagnostic apparatus according to claim 2, wherein said computing means computes the difference between the inside radii of the blood vessel based on the inside radii of the blood vessel in the two locations repeatedly measured by said measuring means, and computes, when the difference between the inside radii of the blood vessel becomes a maximum at a certain time in a predetermined period, the elastic modulus of the blood vessel based on the difference between the inside radii of the blood vessel, the inside radius and the thickness of the blood vessel measured at the certain time, the velocity gradient computed from the blood flow velocities measured at the certain time, the predetermined distance, and the predetermined viscosity of blood.

5. A method of measuring a pressure gradient, said method comprising the steps of:

(a) transmitting ultrasonic waves to an object to be inspected and receiving ultrasonic echoes propagating from the object by using an ultrasonic probe including plural ultrasonic transducers, and thereby, measuring an inside radius of a blood vessel within the object and blood flow velocities in plural locations in a radial direction substantially at the same time; and (b) computing a velocity gradient in the radial direction at an inner wall point of the blood vessel by differentiating the blood flow velocities measured at step (a) in the radial direction, and computing the pressure gradient at ends of a predetermined length of the blood vessel based on the computed velocity gradient, the inside radius of the blood vessel measured at step (a), and a predetermined viscosity of blood, wherein step (b) includes computing the pressure gradient ΔP at the ends of the predetermined length "L" of the blood vessel according to the following equation:

$$\Delta P = \frac{2L\mu}{R}\left(\frac{du}{dr}\right)_{r=R}$$

where "u" represents a blood flow velocity, "r" represents displacement in the radial direction of the blood vessel, "R" represents the inside radius of the blood vessel, and "μ" represents the predetermined viscosity of blood.

6. A method of measuring blood vessel elasticity, said method comprising the steps of:

(a) transmitting ultrasonic waves to an object to be inspected and receiving ultrasonic echoes propagating from the object by using an ultrasonic probe including plural ultrasonic transducers, and thereby, measuring inside radii of a blood vessel in two locations spaced at a predetermined distance in a longitudinal direction of the blood vessel, a thickness of the blood vessel in at least one location, and blood flow velocities in plural locations in a radial direction substantially at the same time; and (b) computing a velocity gradient in the radial direction at an inner wall point of the blood vessel by differentiating the blood flow velocities measured at step (a) in the radial direction, and computing the elastic modulus of the blood vessel based on the computed velocity gradient, the inside radius and the thickness of the blood vessel measured at step (a), a difference between the inside radii of the blood vessel in the two locations, the predetermined distance, and a predetermined viscosity of blood, wherein step (b) includes computing the elastic modulus "E" of the blood vessel according to the following equation:

$$E = \frac{2\mu LR}{h\Delta d}\left(\frac{du}{dr}\right)_{r=R}$$

where "u" represents the blood flow velocity, "r" represents displacement in the radial direction of the blood vessel, "h" represents the thickness of the blood vessel, "R" represents the inside radius of the blood vessel, $\Delta d$ represents the difference between inside radii of the blood vessel in the two locations, "L" represents the predetermined length, and "μ" represents the predetermined viscosity of blood.

* * * * *